(12) United States Patent
Cho et al.

(10) Patent No.: US 7,230,010 B2
(45) Date of Patent: Jun. 12, 2007

(54) 1,2,4-TRIAZOLE DERIVATIVE, METHOD FOR PREPARING THE SAME, AND PHARMACEUTICAL COMPOSITION CONTAINING THE SAME

(75) Inventors: Il Hwan Cho, Seoul (KR); Dong Hyun Ko, Gwacheon (KR); Myeong Yun Chae, Seongnam (KR); Taerho Kim, Seongnam (KR); Kyoung Rae Kang, Seoul (KR); Jong Hoon Kim, Anyang (KR); Sung Hak Jung, Seoul (KR); Sang Wook Park, Suwon (KR); Hyung Ok Chun, Gunpo (KR); Hyung Chul Ryu, Yongin (KR); Ji Young Noh, Busan (KR); Hyun Jung Park, Jeonrabuk-do (KR); Jie Eun Park, Wonju (KR); Young Mee Chung, Suwon (KR)

(73) Assignee: CJ Corp. (KR)

( * ) Notice: Subject to any disclaimer, the term of this patent is extended or adjusted under 35 U.S.C. 154(b) by 213 days.

(21) Appl. No.: 10/633,083

(22) Filed: Aug. 1, 2003

(65) Prior Publication Data
US 2004/0106612 A1 Jun. 3, 2004

(30) Foreign Application Priority Data
Nov. 26, 2002 (KR) ...................... 10-2002-0074118

(51) Int. Cl.
*A61K 31/47* (2006.01)
*A61K 31/41* (2006.01)
*C07D 215/06* (2006.01)
*C07D 249/08* (2006.01)

(52) U.S. Cl. ...................... 514/311; 514/383; 546/152; 548/269.4

(58) Field of Classification Search ................ 514/311, 514/383; 546/152; 548/269.4
See application file for complete search history.

(56) References Cited

U.S. PATENT DOCUMENTS

| | | | |
|---|---|---|---|
| 5,466,823 A | 11/1995 | Talley et al. | 548/377.1 |
| 5,633,272 A | 5/1997 | Talley et al. | 514/378 |
| 6,849,652 B1 * | 2/2005 | Cho et al. | 514/383 |

FOREIGN PATENT DOCUMENTS

| | | |
|---|---|---|
| EP | 1 099 695 A1 * | 5/2001 |
| WO | 95/00501 | 1/1995 |

OTHER PUBLICATIONS

"Current Perspective Recent advances in the management of colorectal cancer"; Authors: E. Van Cutsem, M. Dicato, J. Wils; European Journal of Cancer 37; Elsevier Science Ltd.; 2001; pp. 2302-2309.

Monthly Focus: Central & Peripheral Nervous Systems; "Anti-inflammatory drugs: a hope for Alzheimer's disease?"; Authors: Michael Hull, Klaus Lieb & Bernd L. Fiebich; Asley Publications Ltd.; 2000; pp. 671-683.
News and Views; "Towards a better aspirin"; Author: John Vane; Nature, vol. 367; Jan. 20, 1994; pp. 215-216.
Meeting Report; "COX-1 and COX-2: Toward the Development of More Selective NSAIDs"; Authors: Bruno Battistini, Regina Botting and Y.S. Bakhle; DN & P 7 (8); Oct. 1994; pp. 501-512.
Chapter 19; "Selective Cycloozygenase Inhibitors"; Authors: David B. Reitz and Karen Seibert; Annual Reports in Medicinal Chemistry-30; Academic Press, Inc.; 1995; pp. 179-188.
Pergamon; "Synthesis and Biological Evaluation of 2, 3-Diarylthiophenes as Selective COX-2 and COX-1 Inhibitors"; Authors: Yves Leblanc, Jacques Yves Gauthier, Diane Ethier, Jocelyne Guay, Joseph Mancini, Denis Riendeau, Philip Tagari, Philip Vichers, Elizabeth Wong and Petpiboon Prasit; Bioorganic & Medicinal Chemistry Letters, vol. 5, No. 18; Elsevier Science Ltd.; 1995; pp. 2123-2128.
"Synthesis and Biological Evaluation of the 1, 5-Diarylpyrazole Class of Cycloozygenase-2 Inhibitors: Identification of 4-[5-(4-Methylphenyl)-3-(trifluoromethyl)-1H-pyrazol-1-yl] benzenesulfonamide (SC-58635, Celecoxib)"; Authors: Thomas D. Penning, et al.; Journal of Medicinal Chemistry vol. 40, No. 9; American Chemical Society; 1997; pp. 1347-1365.

* cited by examiner

*Primary Examiner*—James O. Wilson
*Assistant Examiner*—Ebenezer Sackey
(74) *Attorney, Agent, or Firm*—Cantor Colburn LLP

(57) ABSTRACT

A 1,2,4-triazole derivative of formula 1 or a non-toxic salt thereof, a preparation method thereof, and a pharmaceutical composition containing the derivative or the salt as an active ingredient are provided:

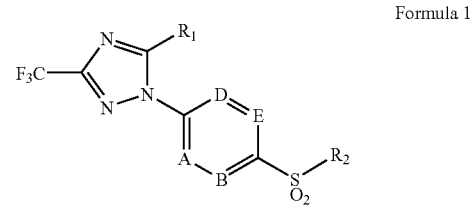

Formula 1 wherein:

$R_1$ represents naphthyl, indolyl, benzofuranyl, benzothienyl, benzimidazolyl, benzothiazolyl, benzotriazolyl, benzooxazolyl, quinolinyl, or isoquinolinyl; wherein, $R_1$ is optionally substituted at a substitutable position with one or more radicals independently selected from halogen, hydroxy, nitro, $C_1$-$C_6$ alkyl, $C_1$-$C_6$ haloalkyl, $C_1$-$C_6$ alkoxy, $C_1$-$C_6$ haloalkoxy, cyano, amino, monoalkylamino, and dialkylamino;

$R_2$ represents methyl or amino; and

A, B, E, and D each independently represent carbon or nitrogen.

2 Claims, No Drawings

1,2,4-TRIAZOLE DERIVATIVE, METHOD FOR PREPARING THE SAME, AND PHARMACEUTICAL COMPOSITION CONTAINING THE SAME

This U.S. non-provisional application claims priority under 35 U.S.C. §119 to Korean Patent Application No. 2002-74118, filed on Nov. 26, 2002, in the Korean Intellectual Property Office, the contents of which are incorporated herein by reference in its entirety.

BACKGROUND OF THE INVENTION

1. Field of the Invention

The present invention relates to a 1,2,4-triazole derivative or a non-toxic salt thereof, a method for preparing the same, and a pharmaceutical composition containing the same as an active ingredient.

2. Description of the Related Art

Most nonsteroidal antiinflammatory agents are responsible for blocking enzyme, cyclooxygenase (COX) or prostaglandin G/H synthase, to reduce inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that can be easily induced by mitogen, endotoxin, hormone, growth factor, or cytokine.

Prostaglandin is a potent mediator for various pathological and physiological processes. The COX-1 plays important physiological roles such as in the release of endogenous prostaglandin, the maintenance of the shape and the function of stomach, and the blood circulation in the kidney. On the other hand, the COX-2 is induced by an inflammatory factor, hormone, a growth factor, or cytokine. Therefore, the COX-2 is involved in pathological processes of prostaglandin, unlike the constitutive COX-1. In this regard, selective inhibitors of the COX-2 produce fewer and less side effects in terms of action mechanism in comparison with conventional nonsteroidal antiinflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, they help in preventing premature birth, menstrual irregularity, asthma, and eosinophilic disease.

Recently, it was reported that nonsteroidal antiinflammatory agents are effective in treating large intestine cancer [*European Journal of Cancer*, Vol 37, p 2302, 2001], prostate cancer [*Urology*, Vol 58, p 127, 2001], and dementia [*Exp. Opin. Invest. Drugs*, Vol 9, p 671, 2000].

In addition, it is anticipated that selective inhibitors of the COX-2 would be effective in treating osteoporosis and glaucoma. Utility of selective inhibitors of the COX-2 is well described in publications [John Vane, "Towards a Better Aspirin" in *Nature*, Vol. 367, pp 215-216, 1994; Bruno Battistini, Regina Botting and Y. S. Bakhle, "COX-1 and COX-2: Toward the Development of More Selective NSAIDs" in *Drug News and Perspectives*, Vol. 7, pp 501-512, 1994; David B. Reitz and Karen Seibert, "Selective Cyclooxygenase Inhibitors" in *Annual Reports in Medicinal Chemistry*, James A. Bristol, Editor, Vol. 30, pp 179-188, 1995].

Various selective COX-2 inhibitors having different structures are known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings. An initial substance having such diaryl heterocyclic structure is Dup697 [*Bioorganic & Medicinal Chemistry Letters*, Vol 5, p 2123, 1995]. Since then, SC-58635 having a pyrazol ring (*Journal of Medicinal Chemistry*, Vol 40, p 1347, 1997) and MK-966 having a furanone ring (WO 95/00501) were discovered as derivatives of the Dup697.

One selective COX-2 inhibitor, Celecoxib of formula 23 is disclosed in U.S. Pat. No. 5,466,823. The Celecoxib is a substituted pyrazolyl benzenesulfonamide derivative.

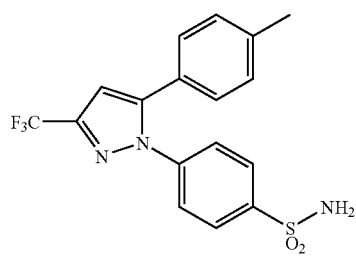

Formula 23

Another selective COX-2 inhibitor, Rofecoxib of formula 24 is disclosed in WO 95/00501. The Rofecoxib has a diaryl heterocyclic structure with a central furanone ring.

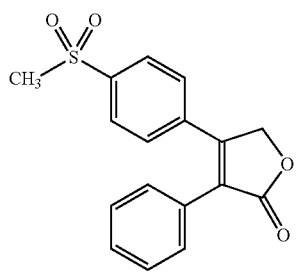

Formula 24

Valdecoxib of formula 25 as another selective COX-2 inhibitor is disclosed in U.S. Pat. No. 5,633,272. The Valdecoxib has a phenylsulfonamide moiety with a central isoxazole ring.

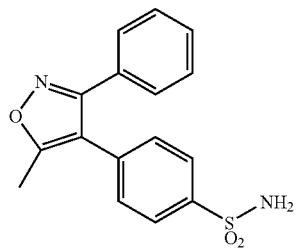

Formula 25

The selective COX-2 inhibitors of formulas 23 to 25 are effective inflammatory therapeutic agents with fewer and less side effects in comparison with conventional nonsteroidal antiinflammatory agents.

SUMMARY OF THE INVENTION

An aspect of the present invention provides a 1,2,4-triazole derivative of formula 1 or a non-toxic salt thereof.

Another aspect of the present invention provides a method for preparing a 1,2,4-triazole derivative or a non-toxic salt thereof.

Another aspect of the present invention provides a pharmaceutical composition comprising a 1,2,4-triazole derivative or a non-toxic salt thereof as an active ingredient for the treatment of fever, pain, and inflammation.

Yet another aspect of the present invention provides a pharmaceutical composition comprising a 1,2,4-triazole derivative or a non-toxic salt thereof as an active ingredient for the treatment of cancers and dementia.

DETAILED DESCRIPTION OF THE INVENTION

According to an aspect of the present invention, there is provided a 1,2,4-triazole derivative represented by formula 1:

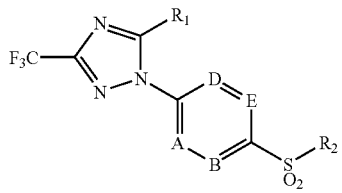

Formula 1 wherein:

$R_1$ represents naphthyl, indolyl, benzofuranyl, benzothienyl, benzimidazolyl, benzothiazolyl, benzotriazolyl, benzooxazolyl, quinolinyl, or isoquinolinyl; wherein, $R_1$ is optionally substituted at a substitutable position with one or more radicals independently selected from halogen, hydroxy, nitro, $C_1$-$C_6$ alkyl, $C_1$-$C_6$ haloalkyl, $C_1$-$C_6$ alkoxy, $C_1$-$C_6$ haloalkoxy, cyano, amino, monoalkylamino, and dialkylamino;

$R_2$ represents methyl or amino; and

A, B, E, and D each independently represent carbon or nitrogen;

or a non-toxic salt thereof.

Preferably, the $R_1$ represents naphthyl, indolyl, benzofuranyl, quinolinyl, or indolyl substituted with $C_1$-$C_6$ alkyl.

The 1,2,4-triazole derivative of formula 1 may be present in a form of a non-toxic salt. The term, "non-toxic salt" as used herein refers to a pharmaceutically acceptable, toxin-free salt, including an organic salt and an inorganic salt.

The Inorganic salt of the 1,2,4-triazole derivative of formula 1 includes an inorganic salt of aluminum, ammonium, calcium, copper, iron, lithium, magnesium, manganese, potassium, sodium, or zinc but is not limited thereto. Preferably, an inorganic salt of ammonium, calcium, potassium, or sodium is used.

The organic salt of the 1,2,4-triazole derivative of formula 1 includes an organic amine salt of primary, secondary, or tertiary amine, substituted amine that is present in nature, or cyclic amine, or a salt of a basic ion exchange resin but is not limited thereto. Examples of the salt of a basic ion exchange resin include, but are not limited to, a salt of arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpyperidine, N-methylglucamine, glutamine, glucosamine, histidine, hydroamine, N-(2-hydroxyethyl)pyperidine, N-(2-hydroxyethyl)pyrrolidine, isopropylamine, lysine, methylglucamine, morpholine, piperazine, piperidine, polyamine resin, procaine, purine, theobromine, triethylamine, trimethylamine, tripropylamine, and tromethamine.

The 1,2,4-triazole derivative of formula 1 may be present in a form of an organic acid salt or an inorganic acid salt.

Examples of the organic acid salt or the inorganic acid salt of the 1,2,4-triazole derivative of formula 1 include, but are not limited to, a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, icethionic acid, lactic acid, maleic acid, malic acid, madelic acid, methane sulfonic acid, mucinic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. Preferably, a salt of succinic acid, hydrobromic acid, hydrochloric acid, maleic acid, methanesulfonic acid, phosphoric acid, sulfuric acid, or tartaric acid is used.

The 1,2,4-triazole derivative of the present invention preferably includes:

1-(4-methylsulfonylphenyl)-5-(naphthalene-2-yl)-3-trifluoromethyl-1H-1,2,4-triazole;

5-(benzofuran-2-yl)-1-(4-methylsulfonylphenyl)-3-trifluoromethyl-1H-1,2,4-triazole;

2-[2-(4-methylsulfonylphenyl)-5-trifluoromethyl-2H-1,2,4-triazole-3-yl]-1H-indole;

1-methyl-2-[2-(4-methylsulfonylphenyl)-5-trifluoromethyl-2H-1,2,4-triazole-3-yl]-1H-indole;

1-methyl-3-[2-(4-methylsulfonylphenyl)-5-trifluoromethyl-2H-1,2,4-triazole-3-yl]-1H-indole;

2-[2-(4-methylsulfonylphenyl)-5-trifluoromethyl-2H-1,2,4-triazole-3-yl]quinoline;

4-[5-(naphthalene-2-yl)-3-trifluoromethyl-1,2,4-triazole-1-yl]benze nesulfonamide; and 5-methanesulfonyl-2-[5-(naphthalene-2-yl)-3-trifluoromethyl-1,2,4-triazole-1-yl]pyridine.

According to another aspect of the present invention, there is provided an amidrazone derivative as an intermediate for the synthesis of the 1,2,4-triazole derivative of formula 1, as represented by formula 4:

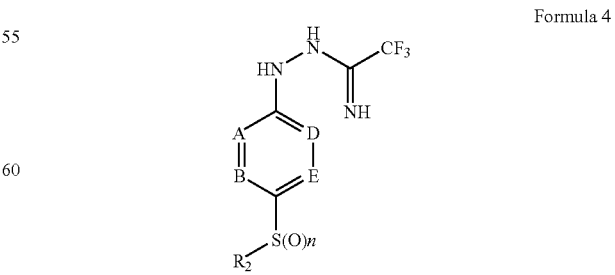

Formula 4 wherein, $R_2$, A, B, E, and D are as defined in formula 1 and n is an integer of 0 to 2.

According to another aspect of the present invention, there is provided a method for preparing a 1,2,4-triazole derivative of formula 1 or a non-toxic salt thereof, comprising reacting an amidrazone derivative of formula 4a with an acyl chloride of formula 5 in the presence of a base:

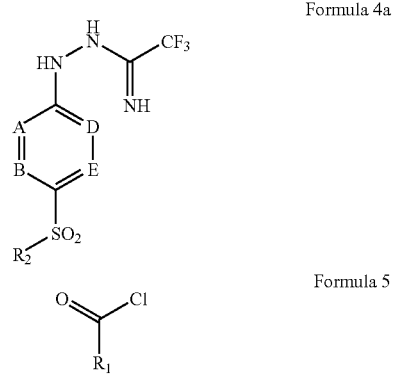

Formula 4a

Formula 5 wherein, $R_1$, $R_2$, A, B, E, and D are as defined in formula 1.

According to another aspect of the present invention, there is provided a method for preparing a 1,2,4-triazole derivative of formula 1 or a non-toxic salt thereof, comprising reacting an amidrazone derivative of formula 4b with an acyl chloride of formula 5 in the presence of a base and oxidizing the resultant compound:

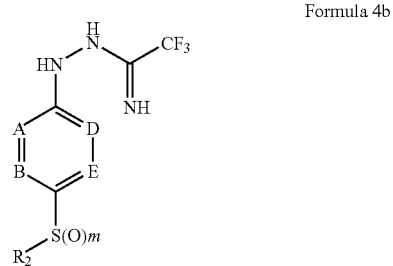

Formula 4b wherein, $R_2$, A, B, E, and D are as defined in formula 1, and m is 0 or 1.

The aforementioned reactions to form a 1,2,4-triazole are preferably carried out in a polar solvent. Examples of the polar solvent include DMF, dioxane, DMSO, methylpyrrolidinone, or m-xylene.

The reactions are preferably carried out at −10° C. to 110° C. A reaction time is determined depending on reactants. Generally, the reaction time lasts 10 minutes to 36 hours.

When the reactions are completed, the reaction resultants are extracted by adding water and an organic solvent such as ethyl acetate, dichloromethane, tetrahydrofuran, and ether, to remove salts. The crude extracts are purified by silica gel column chromatography to give final products.

The base may be an organic base or an inorganic base. Among the organic base, preferably triethyl amine, trimethyl amine, tripropyl amine, pyridine, or imidazole is used. Among the inorganic base, preferably sodium acetate, sodium hydroxide, sodium hydride, potassium hydroxide, sodium carbonate, or potassium carbonate is used.

The oxidative reaction is preferably carried out in dichloromethane in the presence of an oxidizing agent. Preferably, MMPP (Magnesium monoperoxyphthalate hexahydrate), MCPBA (m-chloroperoxybenzoic acid), or Oxone (potassium peroxymonosulfate) is used as an oxidizing agent.

The said compound of formula 4 may be prepared by reacting a hydrazine derivative of formula 2 with a trifluoroacetimidine of formula 3 in the presence of a base:

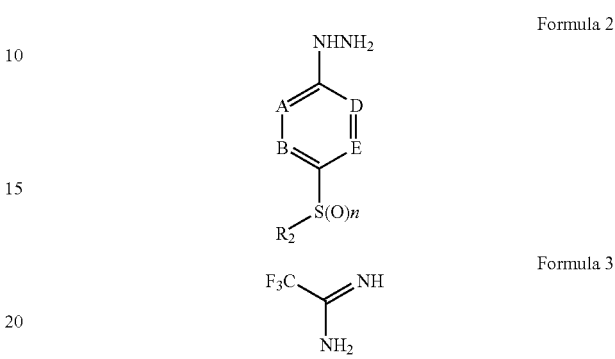

Formula 2

Formula 3 wherein, $R_2$, A, B, E, D, and n are as defined in formula 1.

The aforementioned reactions are preferably carried out in methanol or a mixed solvent of THF and methanol.

The reactions are preferably carried out at −10° C. to 66° C. A reaction time is determined depending on reactants. Generally, the reaction time lasts 10 minutes to 24 hours.

When the reactions are completed, the reaction resultants are extracted by adding water and an organic solvent such as ethyl acetate, dichloromethane, tetrahydrofuran, and ether, to remove salts. The crude extracts are purified by silica gel column chromatography to give final products.

The base to be used herein is an organic base or an inorganic base. Among the organic base, preferably triethyl amine, trimethyl amine, tripropyl amine, pyridine, or imidazole is used. Among the inorganic base, preferably sodium acetate, sodium hydroxide, sodium hydride, potassium hydroxide, sodium carbonate, or potassium carbonate is used. More preferably, triethylamine is used.

When all the said reactions are finished, the separation and purification of the reaction products can be performed by chromatography, recrystallization, or other processes, which are conventionally used in the relevant field.

The method for preparing a compound of formula 1 can be expressed serially by the following reaction formula 1.

Reaction formula 1

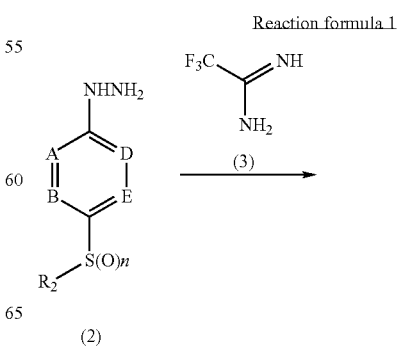

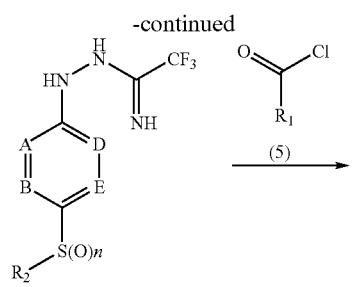

(4)

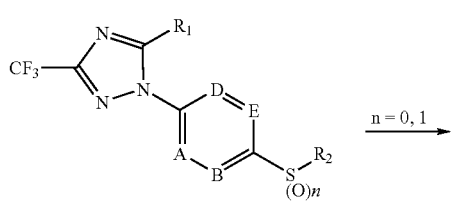

(6)

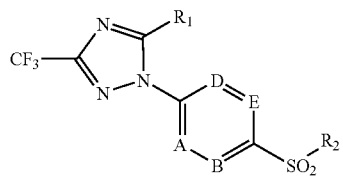

(1)

wherein, $R_1$, $R_2$, A, B, E, D, and n are as defined in formula 1.

4-Hydrazinobenzenesulfonamide hydrochloride of the hydrazine derivatives used in the above reaction may be purchased from the Maybridge corporation, and the other hydrazine derivatives may be prepared as a hydrochloric acid salt or free form according to the methods which are known in the relevant field. The methods for preparing several representative hydrazine derivatives are represented by the following reaction formula 2 to 4.

Reaction formula 2

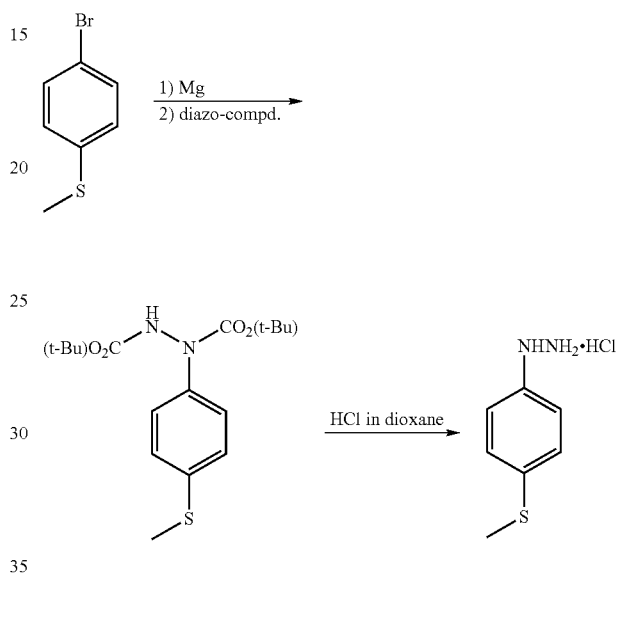

4-Bromothioanisole is reacted with magnesium to form a Grignard compound, which is followed by the reaction with diazocompound and then hydrochloride to obtain a hydrazine derivative hydrochloride.

Reaction formula 3

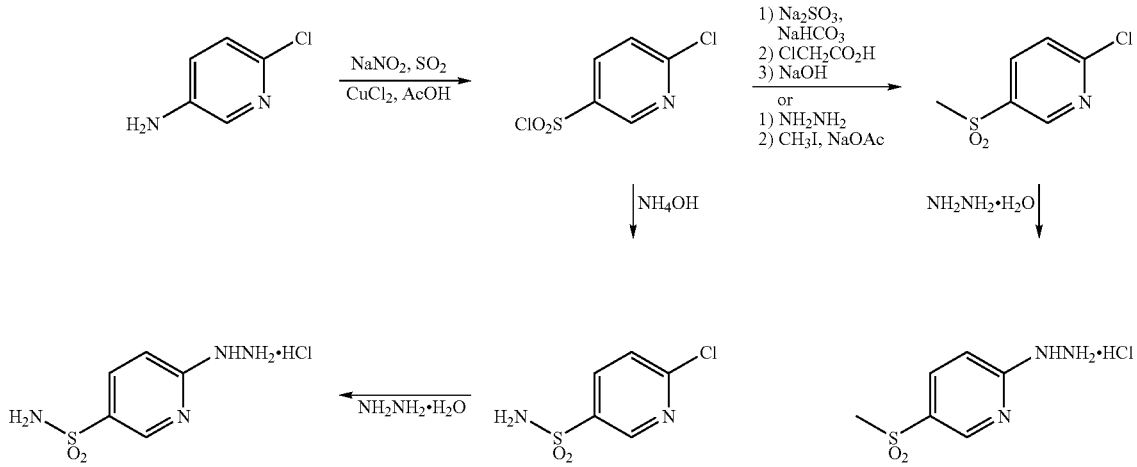

A pyridine derivative is reacted with hydrazine monohydrate directly to obtain a 2-hydrazinopyridine derivative.

Reaction formula 4

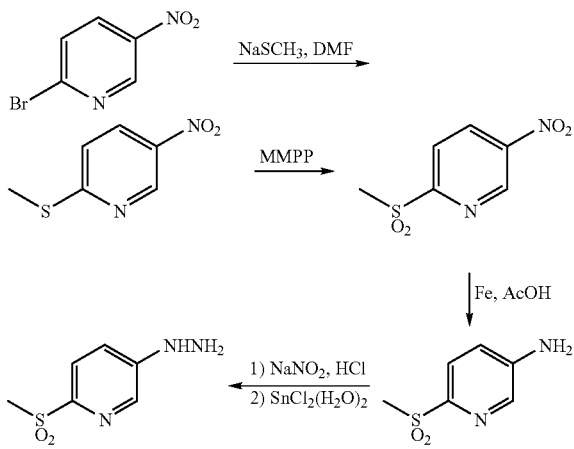

A 3-hydrazinopyridine derivative may be obtained by reducing nitro group into amine group and then introducing hydrazine group.

The method for preparing a compound according to the present invention is not limited to the description hereof, and a compound according to the present invention may be prepared by combining several methods described herein or disclosed in publications, which is conventionally known to a skilled person in the relevant field.

According to another aspect of the present invention, there is provided a pharmaceutical composition comprising a therapeutically effective amount of a 1,2,4-triazole derivative of formula 1 or a non-toxic salt thereof as an active ingredient and a pharmaceutically acceptable carrier for treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an antiinflammatory agent, with reduced side effects.

Conventional nonsteroidal antiinflammatory agents non-selectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and antiinflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal antiinflammatory agents. In particular, due to the reduction of the side effects of conventional nonsteroidal antipyretics, analgesics, and antiinflammatory agents, the pharmaceutical composition of the present invention is useful in treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly useful in treating osteoarthritis and rheumatoid arthritis which require high dosage of nonsteroidal antiinflammatory agents.

The pharmaceutical composition of the present invention can be administered in the form of an adult dosage of 1 mg/day to 1000 mg/day of the compound of formula 1. An adequate dosage is determined depending on the degree of disease severity.

According to yet another aspect of the present invention, there is provided a pharmaceutical composition comprising a therapeutically effective amount of a 1,2,4-triazole derivative of formula 1 or a non-toxic salt thereof and a pharmaceutically acceptable carrier for the treatment of cancers and dementia.

Recently, it was reported that nonsteroidal antiinflammatory agents are effective in the treatment of large intestine cancer [*European Journal of Cancer*, Vol 37, p 2302, 2001], prostate cancer [*Urology*, Vol 58, p 127, 2001], and dementia [*Exp. Opin. Invest. Drugs*, Vol 9, p 671, 2000]. Therefore, it is understood that the pharmaceutical composition of the present invention as a nonsteroidal antiinflammatory agent can also be used for the treatment of these diseases.

The pharmaceutical composition of the present invention can be administered in the form of an adult dosage of 1 mg/day to 1000 mg/day of the compound of formula 1 or a non-toxic salt thereof. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscular injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

A plasticizer suitable for the coating agent is citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed in Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustration and thus the present invention is not limited to or by them.

EXAMPLE 1

N-(4-methylsulfanylphenyl)trifluoroacetamidrazone

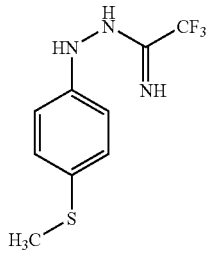

Formula 6

1.0 g (5.24 mmole) of 4-methylsulfanylphenylhydrazine hydrochloride was dissolved in a mixed solution (methanol:tetrahydrofuran=1:1), and 0.8 ml (5.76 mmole) of triethylamine was added thereto and stirred at an ambient temperature. Afterwards, 0.90 g (6.81 mmole) of trifluoroacetimidine (85%) was added dropwise to the solution and stirred at the ambient temperature for 24 hours. When the reaction was completed, water and ethyl acetate were added. Thereafter, the water layer was extracted with ethyl acetate twice, and the organic layer was washed with saturated sodium chloride solution once before being dried on anhydrous magnesium sulfate. The resultant was filtered under reduced pressure and purified by HPLC (ethyl acetate:n–hexane=1:4) to give 0.88 g of the title compound as a liquid (yield 67%).

$^1$H-NMR(400 MHz,CDCl$_3$) δ2.55(s,3H), 5.45(s,2H,br), 7.40(d,2H,J=8.0 Hz), 7.60(d,2H,J=8.0 Hz), 9.70(s, 1H)

EXAMPLE 2

N-(5-methylsulfonylpyridine-2-yl)trifluoroacetamidrazone

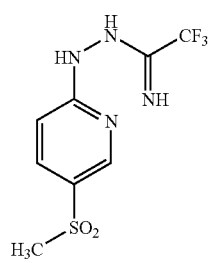

Formula 7

205 mg (yield 54%) of the title compound as a solid was prepared in the same manner as in Example 1 except using 300 mg (1.34 mmol) of 4-methylsulfonylpyridine-2-yl hydrazine hydrochloride instead of 5-methylsulfanylphenyl hydrazine hydrochloride.

$^1$H-NMR(400 MHz,CDCl$_3$) δ2.90(s,3H), 5.65(s,2H,br), 6.95(dd, 1H,J$_1$=9.0 Hz, J$_2$=2.8 Hz), 7.80(dd, 1H,J$_1$=9.0 Hz,J$_2$=2.0 Hz), 9.70(d,1H,J=2.8 Hz), 9.75(s,1H)

EXAMPLE 3

N-(2-methylsulfonylpyridine-5-yl)trifluoroacetamidrazone

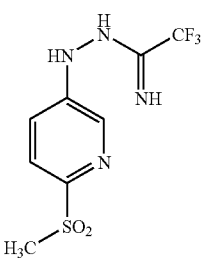

Formula 8

194 mg (yield 51%) of the title compound as a solid was prepared in the same manner as in Example 1 except using 300 mg (1.34 mmol) of 2-methylsulfonylpyridine-5-yl hydrazine hydrochloride instead of 4-methylsulfanylphenyl hydrazine hydrochloride.

$^1$H-NMR(400 MHz,CDCl$_3$) δ3.35(s,3H), 5.65(s,2H,br), 6.95(dd,1H,J$_1$=9.0 Hz, J$_2$=2.8 Hz), 7.80(dd,1H,J$_1$=9.0 Hz,J$_2$=2.0 Hz), 9.70(d,1H,J=2.8 Hz), 9.75(s,1H)

EXAMPLE 4

1-(4-methylthiophenyl)-5-(naphthalene-2-yl)-3-trifluoromethyl-1H-1,2,4-triazole

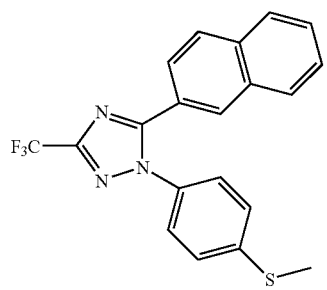

Formula 9

N-(4-methylthiophenyl)trifluoroacetamidrazone prepared in the above example 1 was dissolved in 5 ml of 1,4-dioxane, and 0.08 ml (0.97 mmole) of pyridine was added dropwise thereto and stirred at an ambient temperature for 10 minutes. Afterwards, 185 mg (0.97 mmole) of 2-naphtoyl chloride was added dropwise thereto and stirred by refluxing at the boiling point for 24 hours. When the reaction was completed, the reaction mixture was cooled to the ambient temperature and water and ethyl acetate were added. The water layer was extracted with ethyl acetate twice, and the organic layer was washed with saturated sodium chloride solution once and was dried on anhydrous magnesium sulfate and was filtered under reduced pressure. The resultant was purified by column chromatography (ethyl acetate: n–hexane=1:4) to give 220 mg of the title compound as an oil (yield 65%).

$^1$H-NMR(400 MHz,CDCl$_3$) 2.35(s,3H), 7.20(d,2H,J=8.0 Hz), 7.31-7.35(m,2H), 7.40(d,2H,J=8.0 Hz), 7.49-7.51(m,1H), 7.70-7.90(m,4H)

EXAMPLE 5

5-(benzofuran-2-yl)-1-(4-methylthiophenyl)-3-trifluoromethyl-1H-1,2,4-triazole

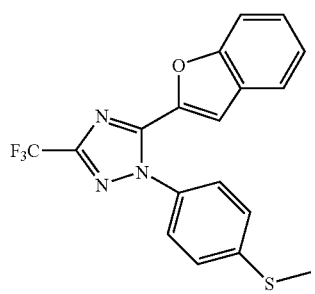

Formula 10

240 mg (yield 73%) of the title compound as a solid was prepared in the same manner as in Example 4 except using 175 mg (0.97 mmol) of benzofuran-2-carbonylchloride instead of 2-naphtoylchloride.

$^1$H-NMR(400 MHz,CDCl$_3$) 2.35(s,3H), 7.20(d,2H,J=8.7 Hz), 7.30-7.42(m,4H), 7.45(d,2H,J=8.7 Hz), 7.68(d,1H, J=6.7 Hz)

EXAMPLE 6

2-[2-(4-methylthiophenyl)-5-trifluoromethyl-2H-1,2,4-triazole-3-yl]-1H-indole

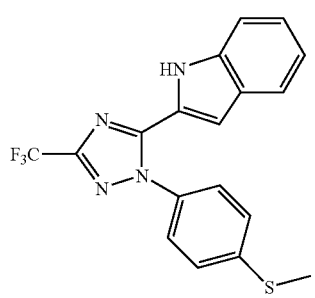

Formula 11

160 mg (yield 48%) of the title compound as a solid was prepared in the same manner as in Example 4 except using 175 mg (0.97 mmol) of 1H-indole-2-carbonylchloride instead of 2-naphtoylchloride.

$^1$H-NMR(400 MHz,CDCl$_3$) 2.35(s,3H), 6.30(d,1H,J=0.6 Hz), 7.20(d,2H,J=8.7 Hz), 7.25(t,1H,J=7.9 Hz), 7.35(t,1H,J=7.9 Hz), 7.45(d,2H,J=8.7 Hz), 7.45(t,1H,J=8.3 Hz), 7.53 (t, 1H,J=8.3 Hz), 9.23(s,1H,br)

EXAMPLE 7

1-methyl-2-[2-(4-methylthiophenyl)-3-trifluoromethyl-2H-1,2,4-triazole-3-yl]-1H-indole

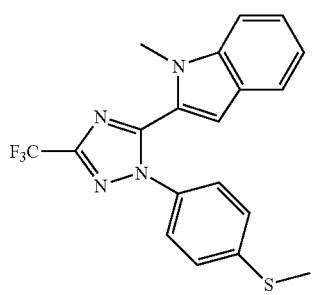

Formula 12

162 mg (yield 52%) of the title compound as a solid was prepared in the same manner as in Example 4 except using 188 mg (0.97 mmol) of 1-methyl-1H-indole-2-carbonylchloride instead of 2-naphtoyl chloride.

$^1$H-NMR(400 MHz,CDCl$_3$) 2.35(s,3H), 4.00(s,3H), 6.41 (d,1H,J=0.6 Hz), 7.15-7.20(m,1H), 7.23(d,2H,J=8.7 Hz), 7.35-7.45(m,2H), 7.46(d,2H,J=8.7 Hz), 7.55(d,1H,J=8.1 Hz),

EXAMPLE 8

1-methyl-3-[2-(4-methylthiophenyl)-3-trifluoromethyl-2H-1,2,4-triazole-3-yl]-1H-indole

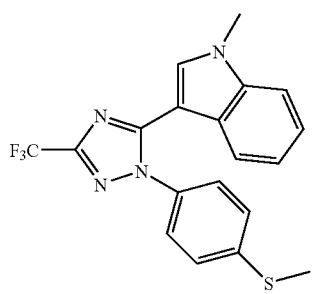

Formula 13

209 mg (yield 64%) of the title compound as a solid was prepared in the same manner as in Example 4 except using 188 mg (0.97 mmol) of 1-methyl-1H-indole-3-carbonylchloride instead of 2-naphtoyl chloride.

$^1$H-NMR(400 MHz,CDCl3) 2.35(s,3H), 3.60(s,3H), 6.90 (s,1H), 7.25(d,2H,J=8.7 Hz), 7.40-7.50(m,6H)

EXAMPLE 9

2-[2-(4-methylthiophenyl)-3-trifluoromethyl-2H-1,2,4-triazole-3-yl]quinoline

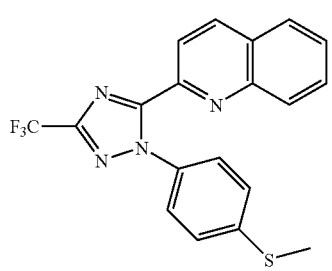

Formula 14

146 mg (yield 47%) of the title compound as a solid was prepared in the same manner as in Example 4 except using 186 mg (0.97 mmol) of quinoline-2-carbonylchloride instead of 2-naphtoyl chloride.

$^1$H-NMR(400 MHz,CDCl$_3$) 2.35(s,3H), 7.25(d,2H, J1=9.1 Hz), 7.45(d,2H,J1=9.1 Hz), 7.54(dd,1H,J1=7.9 Hz,J2=1.2 Hz), 7.60(td,1H,J1=7.9 Hz,J2=1.2 Hz), 7.66(td, 1H,J1=7.9 Hz,J2=1.2 Hz), 7.84(dd,1H,J1=7.9 Hz,J2=1.2 Hz), 8.28(d,1H,J1=8.5 Hz), 8.31(d,1H,J1=8.5 Hz)

EXAMPLE 10

1-(4-methylsulfonylphenyl)-5-(naphthalene-2-yl)-3-trifluoromethyl-1H-1,2,4-triazole

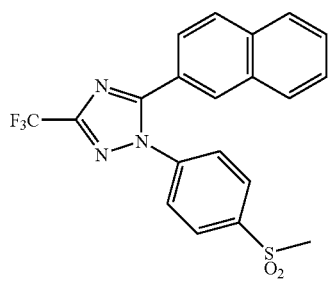

Formula 15

193 mg (0.05 mmole) of 1-(4-methylthiophenyl)-5-(naphthalen-2-yl)-3-trifluoromethyl-1H-1,2,4-triazole was dissolved in a mixed solution (5 ml of dichloromethane and 1 ml of methanol), and 402 mg (0.65 mmole) of MMPP was added dropwise thereto and stirred at an ambient temperature for 5 hours, and then the mixture was filtered and the filtrate was washed with sodium bicarbonate and saturated sodium chloride solution separately once and was dried on anhydrous magnesium sulfate and was filtered under reduced pressure. The resultant was purified by column chromatography (ethyl acetate:n-hexane=2:3) to give 186 mg of the title compound as a solid (yield 89%).

$^1$H-NMR(400 MHz,CDCl3) 2.35(s,3H), 7.31-7.35(m, 2H), 7.49-7.51 (m,1H), 7.70-7.90(m,6H), 8.10(d,2H,J=8.0 Hz)

EXAMPLE 11

5-(benzofuran-2-yl)-1-(4-methylsulfonylphenyl)-3-trifluoromethyl-1H-1,2,4-triazole

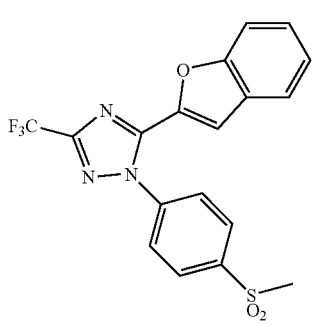

Formula 16

175 mg (yield 86%) of the title compound as a solid was prepared in the same manner as in Example 10 except using 5-(benzofuran-2-yl)-1-(4-methylthiophenyl)-3-trifluoromethyl-1H-1,2,4-triazole instead of 1-(4-methylthiophenyl)-5-(naphthalen-2-yl)-3-trifluoromethyl-1H-1,2,4-triazole.

$^1$H-NMR(400 MHz,CDCl$_3$) 2.35(s,3H), 7.30-7.42(m, 4H), 7.68(d,1H,J=6.7 Hz), 7.80(d,2H,J=8.7 Hz), 8.15(d,2H, J=8.7 Hz)

EXAMPLE 12

2-[2-(4-methylsulfonylphenyl)-5-trifluoromethyl-2H-1,2,4-triazole-3-yl]-1H-indole

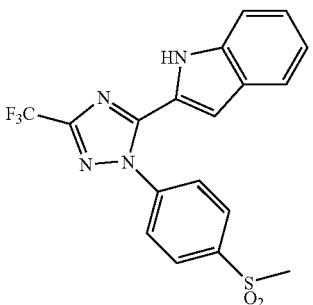

Formula 17

179 mg (yield 88%) of the title compound as a solid was prepared in the same manner as in Example 10 except using 187 mg (0.50 mmole) of 2-[2-(4-metylthiophenyl)-5-trifluoromethyl-2H-1,2,4-triazole-3-yl]-1H-indole instead of 1-(4-methylthiophenyl)-5-(naphthalen-2-yl)-3-trifluoromethyl-1H-1,2,4-triazole.

$^1$H-NMR(400 MHz,CDCl$_3$) 2.35(s,3H), 6.30(d,1H,J=0.6 Hz), 7.25(t,1H,J=7.9 Hz), 7.35(t,1H,J=7.9 Hz), 7.45(t, 1H,J=8.3 Hz), 7.53(t,1H,J=8.3 Hz), 7.89(d,2H,J=8.7 Hz), 8.23(d,2H,J=8.7 Hz)

EXAMPLE 13

1-methyl-2-[2-(4-methylsulfonylphenyl)-5-trifluoromethyl-2H-1,2,4-triazole-3-yl]-1H-indole

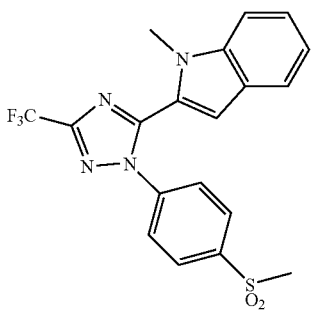

Formula 18

195 mg (yield 93%) of the title compound as a solid was prepared in the same manner as in Example 10 except using 194 mg (0.50 mmole) of 1-methyl-2-[2-(4-methylthiophenyl)-5-trifluoromethyl-2H-1,2,4-triazole-3-yl]-1H-indole instead of 1-(4-methylthiophenyl)-5-(naphthalen-2-yl)-3-trifluoromethyl-1H-1,2,4-triazole.

$^1$H-NMR(400 MHz,CDCl$_3$) 2.35(s,3H), 4.00(s,3H), 6.41 (d,1H,J=0.6 Hz), 7.15-7.20(m,1H), 7.35-7.45(m,2H), 7.55 (d,1H,J=8.1 Hz), 7.72(d,2H,J=8.7 Hz), 8.05(d,2H,J=8.7 Hz)

EXAMPLE 14

1-methyl-3-[2-(4-methylsulfonylphenyl)-5-trifluoromethyl-2H-1,2,4-triazole-3-yl]-1H-indole

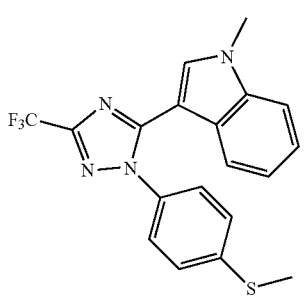

Formula 19

176 mg (yield 85%) of the title compound as a solid was prepared in the same manner as in Example 10 except using 194 mg (0.50 mmole) of 1-methyl-3-[2-(4-methylthiophenyl)-5-trifluoromethyl-2H-1,2,4-triazole-3-yl]-1H-indole instead of 1-(4-methylthiophenyl)-5-(naphthalen-2-yl)-3-trifluoromethyl-1H-1,2,4-triazole.

$^1$H-NMR(400 MHz,CDCl$_3$) 2.35(s,3H), 3.60(s,3H), 6.90 (s,1H), 7.40-7.50(m,4H), 7.80(d,2H,J=8.7 Hz), 8.10 (d,2H, J=8.7 Hz)

EXAMPLE 15

2-[2-(4-methylsulfonylphenyl)-5-trifluoromethyl-2H-1,2,4-triazole-3-yl]quinoline

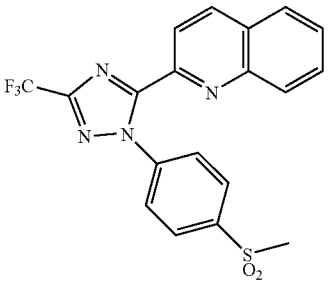

Formula 20

173 mg (yield 83%) of the title compound as a solid was prepared in the same manner as in Example 10 except using 193 mg (0.50 mmol) of 2-[2-(4-methylthiophenyl)-5-trifluoromethyl-2H-1,2,4-triazole-3-yl]quinoline instead of 1-(4-methylthiophenyl)-5-(naphthalen-2-yl)-3-trifluoromethyl-1H-1,2,4-triazole.

$^1$H-NMR(400 MHz,CDCl$_3$) 2.35(s,3H), 7.54(dd,1H, J1=7.9 Hz,J2=1.2 Hz), 7.60(td,1H,J1=7.9 Hz,J2=1.2 Hz), 7.66(td,1H,J1=7.9 Hz,J2=1.2 Hz), 7.80(ddd,2H,J1=9.1 Hz,J2=2.3 Hz,J3=2.0 Hz), 7.84(dd,1H,J1=7.9 Hz,J2=1.2 Hz), 8.08(ddd,2H,J1=9.1 Hz,J2=2.3 Hz,J3=2.0 Hz), 8.28(d, 1H,J1=8.5 Hz), 8.31(d,1H,J1=8.5 Hz)

EXAMPLE 16

4-[5-(naphthalene-2-yl)-3-trifluoromethyl-1,2,4-triazole-1-yl]benzenesulfonamide

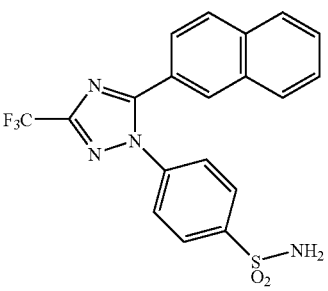

Formula 21

248 mg (0.88 mmol) of N-(4-sulfonamidophenyl)trifluoro acetamidrazone was dissolved in 5 ml of 1,4-dioxane, and 0.08 ml (0.97 mmole) of pyridine was added dropwise thereto and stirred at an ambient temperature for 10 minutes. Afterwards, 185 mg (0.97 mmole) of 2-naphtoyl chloride was added dropwise thereto and stirred by refluxing at the boiling point for 24 hours. When the reaction was completed, the reaction mixture was cooled to the ambient temperature and water and ethyl acetate were added thereto, the water layer was extracted with ethyl acetate twice, and then the organic layer was washed with saturated sodium chloride solution once and was dried on anhydrous magnesium sulfate and was filtered under reduced pressure. The resultant was purified by column chromatography (ethyl acetate:n-hexane=2:3) to give 191 mg of the title compound as a solid (yield 52%).

$^1$H-NMR(400 MHz,CDCl$_3$) 6.32(s,2H), 7.31-7.35(m, 2H), 7.49-7.51(m,1H), 7.70-7.90(m,6H), 8.10(d,2H,J=8.0 Hz)

EXAMPLE 17

5-methanesulfonyl-2-[5-(naphthalene-2-yl)-3-trifluoromethyl-1,2,4-triazole-1-yl]pyridine

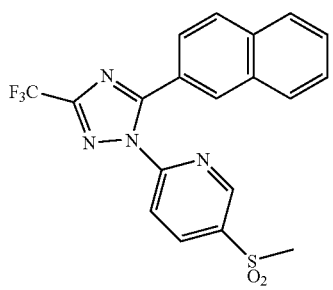

Formula 22

88 mg (yield 42%) of the title compound as a solid was prepared in the same manner as in Example 16 except using 193 mg (0.50 mmol) of N-(5-methylsulfonylpyridine-2-yl)trifluoroacetamidrazone instead of N-(4-sulfonamidophenyl)trifluoroacetamidrazone.

$^1$H-NMR(400 MHz,CDCl$_3$) 3.15(s,3H), 7.45(dd,1H, J1=8.5 Hz,J2=1.8 Hz), 7.55-7.65(m,2H), 7.85-7.93(m,3H), 8.05(dd,1H,J1=8.5 Hz,J2=0.5 Hz), 8.23(d,1H,J=1.1 Hz), 8.45(dd,1H,J1=8.5 Hz,J2=2.5 Hz), 78.83(d,1H,J=2.5 Hz)

Experiments

1. Evaluation of Selective COX-2 Inhibitory Activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 Inhibitory Activity Using U-937

U-937 human lymphoma cells (Korean Cell Line Bank, Seoul, Korea, Accession Number: 21593) were cultured and centrifuged. The collected cells were diluted with HBSS (x1, Hank's balanced salt solution) to a concentration of 1×10$^6$ cells/ml. 1 ml of the dilute cell solution was placed into each well of 12-well plates. 5 µl of 1 µM solution of a test compound in DMSO and 5 µl of DMSO as a control were added to the wells. The wells were incubated in CO$_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 µl of the 1 mM solution of arachidonic acid was added to each well and incubated at CO$_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 Inhibitory Activity Using RAW 264.7 Cell Line

2×10$^6$ cells of RAW 264.7 cell line (Korean Cell Line Bank, Seoul, Korea, Accession Number: 40071) were inoculated into each well of 12-well plates. Each well was treated with 250 µM of aspirin and incubated at 37° C. for 2 hours. After the culture media were replaced with new culture media, the new culture media were treated with a test compound (10 nM) and incubated for 30 minutes. Then, each well was treated with interferon γ (100 units/ml) and lipopolysaccharide (LPS, 100 ng/ml) and incubated for 18 hours. The culture media were transferred to other test tubes. The concentration of PGE2 was quantified by means of the EIA kit (Cayman Chemicals).

2) Test Results

The test results are presented in Table 1 below. The percentages of the COX inhibition were calculated according to the following equation:

% Inhibition=(concentration of PGE2 in test compound-untreated sample−concentration of PGE2 in test compound-treated sample)/(concentration of PGE2 in test compound-untreated sample)×100

TABLE 1

| Cyclooxygenase (COX) Inhibition (%) | | |
| --- | --- | --- |
| Samples | COX-1 (1 µM) | COX-2 (10 nM) |
| Reference (Valdecoxib) | 28.8 | 5.47 |
| Example 10 | 26.2 | 12.3 |
| Example 11 | 24.3 | 10.6 |
| Example 12 | 26.3 | 5.67 |
| Example 13 | 9.8 | 25.7 |
| Example 14 | 21.3 | 6.02 |
| Example 15 | 22.3 | 5.42 |
| Example 16 | 32.9 | 16.3 |
| Example 17 | 10.6 | 23.3 |

3) Evaluation

The in vitro test results about the percentages of the COX-1 and COX-2 inhibition are listed in Table 1.

As shown in Table 1, inhibition (%) ratios of COX-2 to COX-1 in Examples 10 to 17 were equal to or significantly higher than that in the reference, Valdecoxib. This indicates that selective inhibition of COX-2 to COX-1 of the present compound is equal or superior to that of the reference.

The compounds of Examples 10 to 17 exhibited the COX-2 inhibitory activities significantly higher than the reference. Based on this result, it can be seen that the present compounds have reduced side effects due to enhanced selectivity and improved relief effects of fever, pain, and inflammation, compared to the reference.

INDUSTRIAL APPLICABILITY

As apparent from the above description, the present invention provides a 1,2,4-triazole derivative or a non-toxic salt thereof, a preparation method thereof, and a pharmaceutical composition containing the derivative or the salt as an active ingredient. The pharmaceutical composition is effective in reducing fever, pain, and inflammation. In particular, as a result of reduction of the side effects of con ventional nonsteroidal antiinflammatory agents, the pharmaceutical composition is useful for treating patients with peptic ulcer disease, gastritis, regional enteritis, ulcerative colitis, diverticullitis, gastrorrhagia, or hypoprothrombinemia.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A 1,2,4-triazole derivative represented by formula 1:

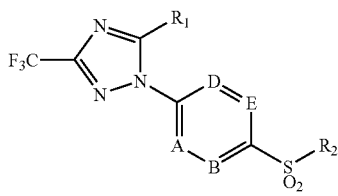

Formula 1 wherein:
$R_1$ represents naphthyl, indolyl, benzofuranyl, quinolinyl, or indolyl substituted with $C_1$-$C_6$ alkyl;
$R_2$ represents methyl or amino; and
A, B, E, and D each independently represent carbon;
or a non-toxic salt thereof.

2. The 1,2,4-triazole derivative according to claim 1, which is selected from the group consisting of:
   1-(4-methylsulfonylphenyl)-5-(naphthalene-2-yl)-3-trifluoromethyl-1H-1,2,4-triazole;
   5-(benzofuran-2-yl)-1-(4-methylsulfonylphenyl)-3-trifluoromethyl-1H-1,2,4-triazole;
   2-[2-(4-methylsulfonylphenyl)-5-trifluoromethyl-2H-1,2,4-triazole-3-yl]-1H-indole;
   1-methyl-2-[2-(4-methylsulfonylphenyl)-5-trifluoromethyl-2H-1,2,4-triazole-3-yl]-1H-indole;
   1-methyl-3-[2-(4-methylsulfonylphenyl)-5-trifluoromethyl-2H-1,2,4-triazole-3-yl]-1H-indole;
   2-[2-(4-methylsulfonylphenyl)-5-trifluoromethyl-2H-1,2,4-triazole-3-yl]-quinoline; and
   4-[5-(naphthalene-2-yl)-3-trifluoromethyl-1,2,4-triazole-1-yl]benzenesulfonamide,
   or a non-toxic salt thereof.

* * * * *